United States Patent
Yokozawa et al.

(10) Patent No.: US 6,418,190 B1
(45) Date of Patent: Jul. 9, 2002

(54) IMAGING PLATE X-RAY DIFFRACTION APPARATUS

(75) Inventors: Yutaka Yokozawa, Akishima; Yuji Ohashi, Tokyo; Katsunari Sasaki, Oume, all of (JP)

(73) Assignees: Japan Science and Technology Corporation; Rigaku Corporation, both of (JP)

( * ) Notice: Subject to any disclaimer, the term of this patent is extended or adjusted under 35 U.S.C. 154(b) by 0 days.

(21) Appl. No.: 09/743,606

(22) PCT Filed: Jul. 16, 1999

(86) PCT No.: PCT/JP99/03844
§ 371 (c)(1),
(2), (4) Date: Jan. 12, 2001

(87) PCT Pub. No.: WO00/04376
PCT Pub. Date: Jan. 27, 2000

(30) Foreign Application Priority Data

Jul. 17, 1998 (JP) .............................. 10-202980

(51) Int. Cl.$^7$ .............................................. G01N 23/207
(52) U.S. Cl. ............................................ 378/81; 378/73
(58) Field of Search ...................... 378/73–81

(56) References Cited

U.S. PATENT DOCUMENTS 3,466,438 A * 9/1969 Abrahamsson ............... 378/81
4,076,981 A * 2/1978 Sparks et al. .................. 378/80
6,285,736 B1 * 9/2001 Dosho .......................... 378/81

FOREIGN PATENT DOCUMENTS

| JP | 58-162847 | 9/1983 |
| JP | 64-147858 | 7/1987 |
| JP | 6-19014 | 1/1994 |
| JP | 6-180297 | 6/1994 |

* cited by examiner

Primary Examiner—Craig E. Church
(74) Attorney, Agent, or Firm—Lorusso & Loud

(57) ABSTRACT

A space-efficient imaging-plate-type X-ray diffraction apparatus featuring an expanded 2θ goniometry range, high speed, high resolution, and design for convenient use is provided. The imaging-plate-type X-ray diffraction apparatus includes an X-ray measurement device composed of an X-ray optical system (5) and a goniometer (1) and is adapted to cause a single-crystal sample (3) to diffract X-rays. A cylindrical imaging plate (21) is disposed vertically so as to record X-rays diffracted by the sample (3), and covering a 2θ goniometry range of −60° to +144°. A drive motor (11) and a transmission mechanism (12) transfer the cylindrical imaging plate vertically; and a rotary reader (20) is disposed so as to be coaxial with the transferred cylindrical imaging plate (21) and is adapted to read data of diffracted X-rays from an inner cylindrical surface of the cylindrical imaging plate (21).

2 Claims, 5 Drawing Sheets

MEASUREMENT RANGE (EXPOSURE AREA)

IMAGING PLATE X-RAY DIFFRACTION APPARATUS

TECHNICAL FIELD

The present invention relates to an imaging-plate-type X-ray diffraction apparatus, and more particularly, to a space-efficient imaging-plate-type X-ray diffraction apparatus featuring a broad exposure area, high speed, high resolution, and convenient design for use.

BACKGROUND ART

Generally, in analysis of crystal structures of organic and inorganic substances, a single crystal of a substance to be analyzed is formed and subjected to X-ray diffraction measurement.

However, future research efforts will require development of apparatus capable of measuring data at high speed and resolution. For example, there is need for use of not only Mo (molybdenum) Kα rays (wavelength: 0.710 angstroms) but also Cu (copper) Kα rays (wavelength: 1.542 angstroms) in measurement by a single X-ray diffraction apparatus.

In order to meet such a need, the following types of apparatus for analyzing the structure of a single crystal by means of X-rays have been developed.

(1) An automatic X-ray single-crystal analyzer capable of measuring three-dimensional spots. The automatic X-ray single-crystal analyzer includes an X-ray generator, a 4-axis goniometer, a scintillation counter mounted on the 2θ-axis of the goniometer, and a computer system for processing diffraction data.

The automatic X-ray single-crystal analyzer can collect every X-ray diffraction datum of a sample, but occupies a large space and needs 3 to 4 days to collect all X-ray diffraction data of a sample because of measurement of three-dimensional spots.

(2) An imaging-plate-type X-ray diffraction apparatus including a cylindrical imaging plate which is disposed horizontally so as to acquire X-ray diffraction data simultaneously to thereby shorten time required to collect X-ray diffraction data.

This imaging-plate-type X-ray diffraction apparatus contributes greatly to the shortening of time required for collection of X-ray diffraction data. However, the 2θ goniometry range of the apparatus is ±60 degrees; i.e., the apparatus is dedicated to measurement through use of Mo Kα rays (wavelength: 0.710 angstroms). When Cu Kα rays (wavelength: 1.542 angstroms) are used, a 2θ goniometry range of at least 0 to 140 degrees is required. In order to acquire this 2θ range, space for access to a crystal must be narrowed significantly, thereby affecting convenience of use.

Thus, in order to carry out measurement through use of Mo Kα rays (wavelength: 0.710 angstroms) as well as Cu Kα rays (wavelength: 1.542 angstroms), a user has no choice but to endure a long time taken for the collection of data by use of the apparatus described above in (1), or to sacrifice convenience of use.

The apparatus described above in (2) is of the horizontal type, involving a problem in that the width is large.

SUMMARY OF THE INVENTION

An object of the present invention is to solve the above-mentioned problems and to provide a space-efficient imaging-plate-type X-ray diffraction apparatus featuring an expanded 2θ goniometry range, high speed, high resolution, and convenient design for use.

To achieve the above object, the present invention provides an imaging-plate-type X-ray diffraction apparatus as described below.

An imaging-plate-type X-ray diffraction apparatus comprises means for causing a set single-crystal sample to diffract X-rays, the means comprising an X-ray optical system and a goniometer, the sample being set on the goniometer; a cylindrical imaging plate disposed vertically so as to record X-rays diffracted by the sample, and covering a 2θ goniometry range of −60° to +144°; transfer means for transferring the cylindrical imaging plate vertically; and a rotary reader disposed so as to be coaxial with the transferred cylindrical imaging plate and adapted to read data of diffracted X-rays from an inner cylindrical surface of the cylindrical imaging plate.

In a preferred embodiment of the imaging-plate-type X-ray diffraction apparatus as described above, the goniometer is disposed at a position located inside the cylindrical imaging plate and corresponding to a lower portion of the cylindrical imaging plate, without mechanically interfering with the X-ray optical system and the cylindrical imaging plate, such that an axis of the sample is positioned vertically.

In the imaging-plate-type X-ray diffraction apparatus as described above in [1], the radiated X-rays are preferably Cu Kα rays.

DESCRIPTION OF THE PREFERRED EMBODIMENTS

An embodiment of the present invention will next be described in detail with reference to the drawings.

Figure 1:
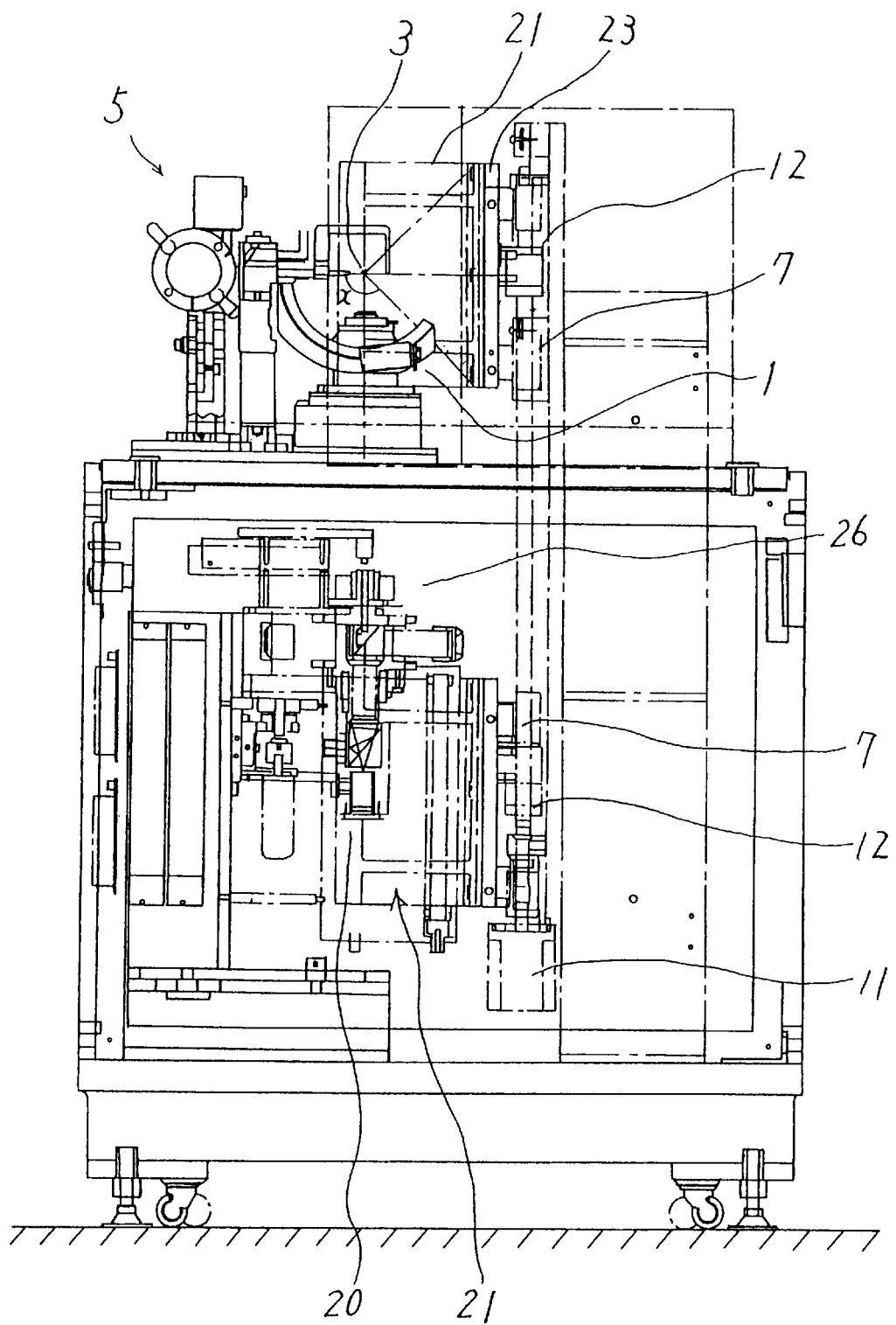
FIG. 1 is a view showing the overall configuration of an imaging-plate-type X-ray diffraction apparatus according to an embodiment of the present invention.
Figure 2:
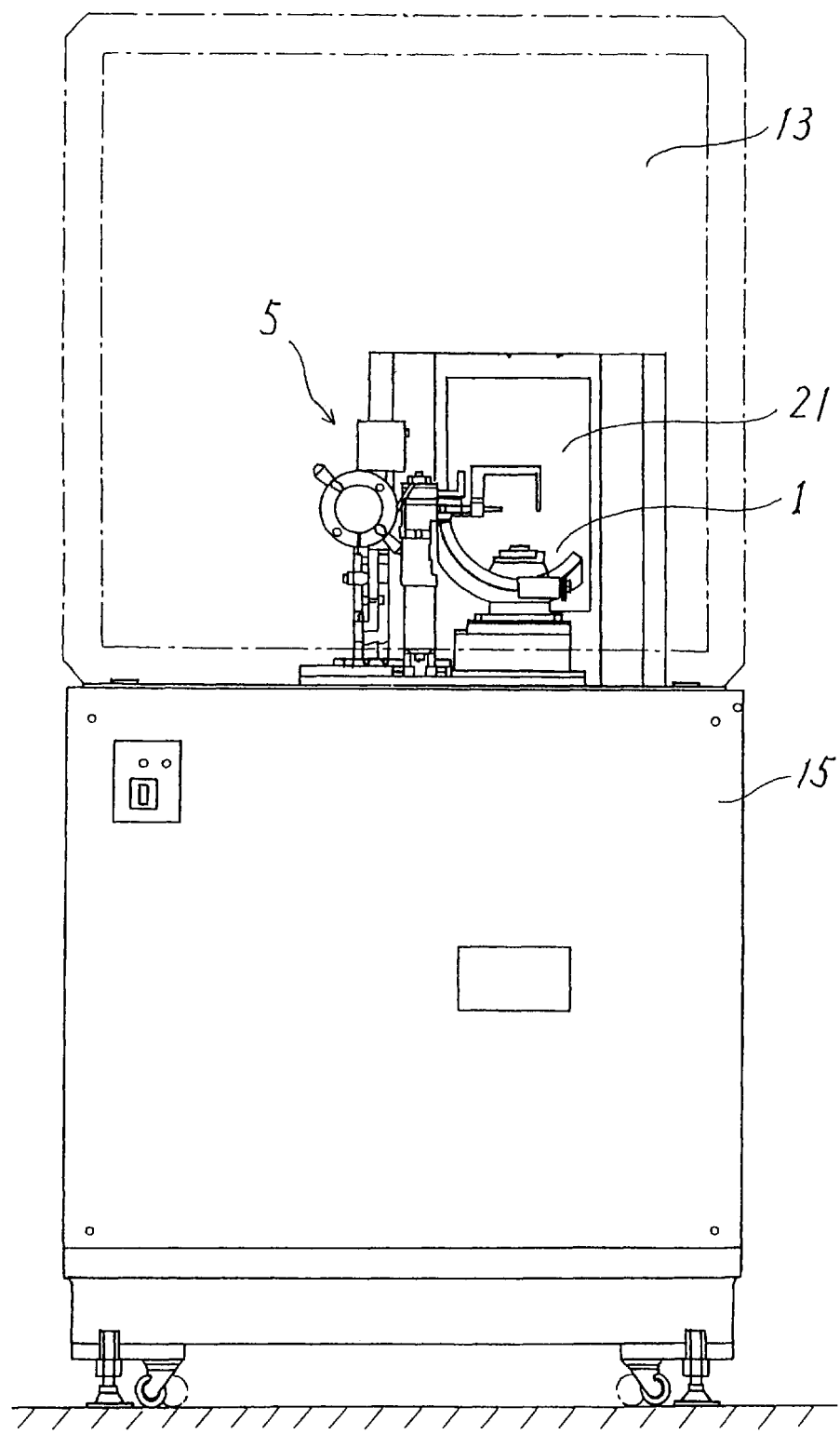
FIG. 2 is a front view of a main portion of the imaging-plate-type X-ray diffraction apparatus according to the embodiment.
Figure 3:
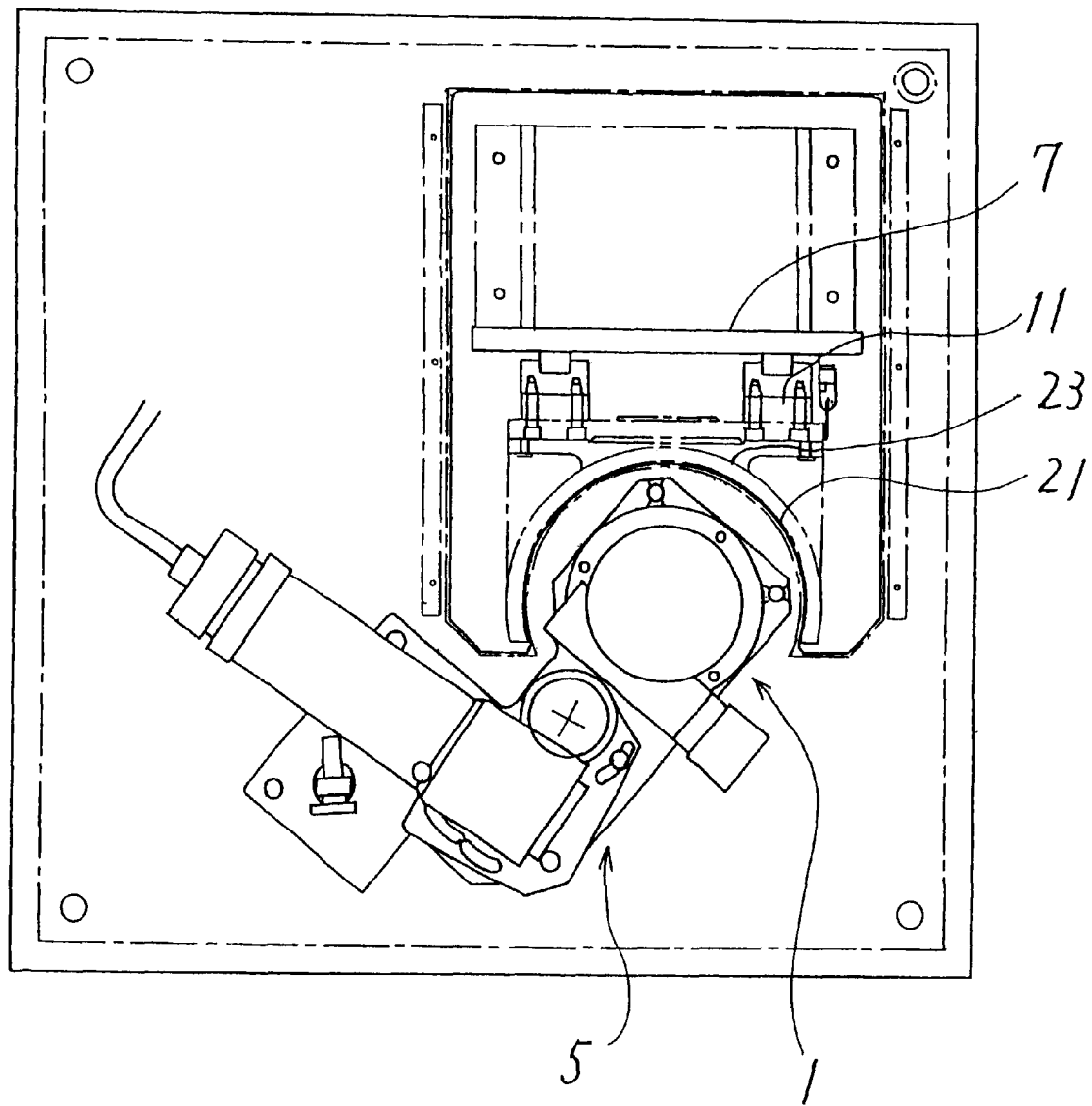
FIG. 3 is a top view of the imaging-plate-type X-ray diffraction apparatus according to the embodiment.

FIG. 1 is a view showing the overall configuration of an imaging-plate-type X-ray diffraction apparatus according to an embodiment of the present invention; FIG. 2 is a front view of a main portion of the imaging-plate-type X-ray diffraction apparatus; and FIG. 3 is a top view showing the imaging-plate-type X-ray diffraction apparatus. Specifications for component parts appearing below are mere examples and should not be construed as limiting the invention.

In these drawings, reference numeral 1 denotes a goniometer on which a crystal 3, which serves as a sample, is set. The crystal 3 can be rotated by 360° in 0.02° steps on the φ-axis, it can be rotated within a range from −15° to 55° in 0.002° steps on the φ-axis, and it can be rotated within a range from −85° to 265° in 0.002° steps on the ω-axis. Accuracy in intersection of the axes is, for example, about 20 μm. The goniometer head employed is a single arcless gonio-head which conforms to the IUCr standard (49 mm type).

Reference numeral 5 denotes an X-ray optical system.

A camera section includes a vertical Weissenberg camera having the following design features: camera length: 127.38 mm; goniometry range 2θ: −60° to +144°; and axial direction: ±45°. The monochromator is a flat graphite crystal and the collimator is 0.3 mm, 0.5 mm, and 0.8 mm double. A beam stopper is disposed immediately behind the crystal. A CCD camera (about 70 magnifications on a magnification monitor) is employed to observe a sample. The layer line screen employed is a screen for 0 layer line (width fixed to 5 mm).

Figure 4:
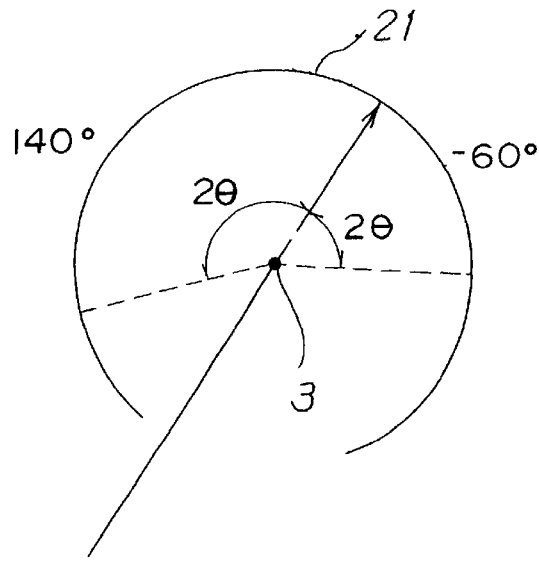
FIG. 4 is a diagram for explaining the available goniometry range for a sample in the embodiment.
Figure 5:
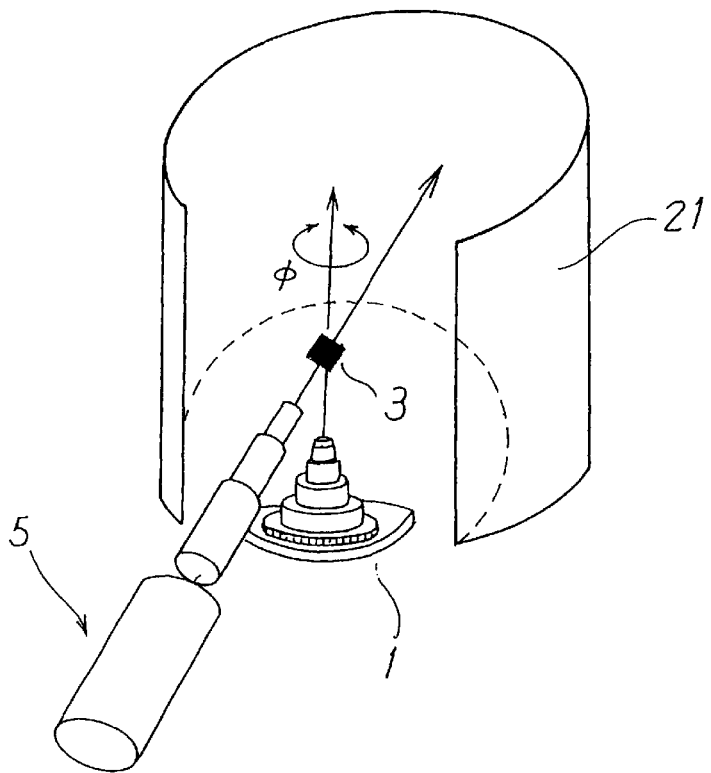
FIG. 5 is a schematic diagram showing a method for detecting (recording) X-rays diffracted by a sample in the embodiment.

As shown in FIGS. 4 and 5, the single crystal 3, which serves as a sample, is set on the goniometer 1 so as to be irradiated with X-rays emitted from the X-ray optical system 5. The single crystal 3 diffracts the X-rays and the thus-diffracted X-rays are recorded on an imaging plate 21.

In FIG. 1, reference numeral 7 denotes a linear guide for transferring vertically downward the imaging plate 21 mounted on a carrier 23; reference numeral 11 denotes a drive motor for transferring the imaging plate 21; and reference numeral 12 denotes a transmission mechanism.

The above-mentioned major components are disposed in a housing 15 of the apparatus. The housing 15 also accommodates a reader 20. Reference numeral 13 denotes a cover which serves as a shield against X-rays generated in the X-ray measurement section.

The rotary reader 20 will next be described. An inner-circumference reading method (reading through rotation of an optical system) is employed. The imaging plate 21 has the following design features: area of detection: 460 mm×255 mm; pixel size: 100×100 μm, 100×105 μm, and 200×200 μm; and number of pixels: 4600×2550, 4600×1700, and 2300×1275. The camera radius is 127.38 mm and the detector is a photoelectric multiplier. The light source for reading is a semiconductor laser (maximum rated output: 25 mW). The dynamic range is 1 to $10^6$ (0 to 1048480). Reading sensitivity is 1-X-ray photons/pixel and output data are at about 23.5 MB/(100×100 μm). The number of IP sheets is one. Reading time is 1500 lines/mm or about 100 sec/(100×100 μm), erasing time is 20 sec, and duty time is about 140 sec.

Figure 6:
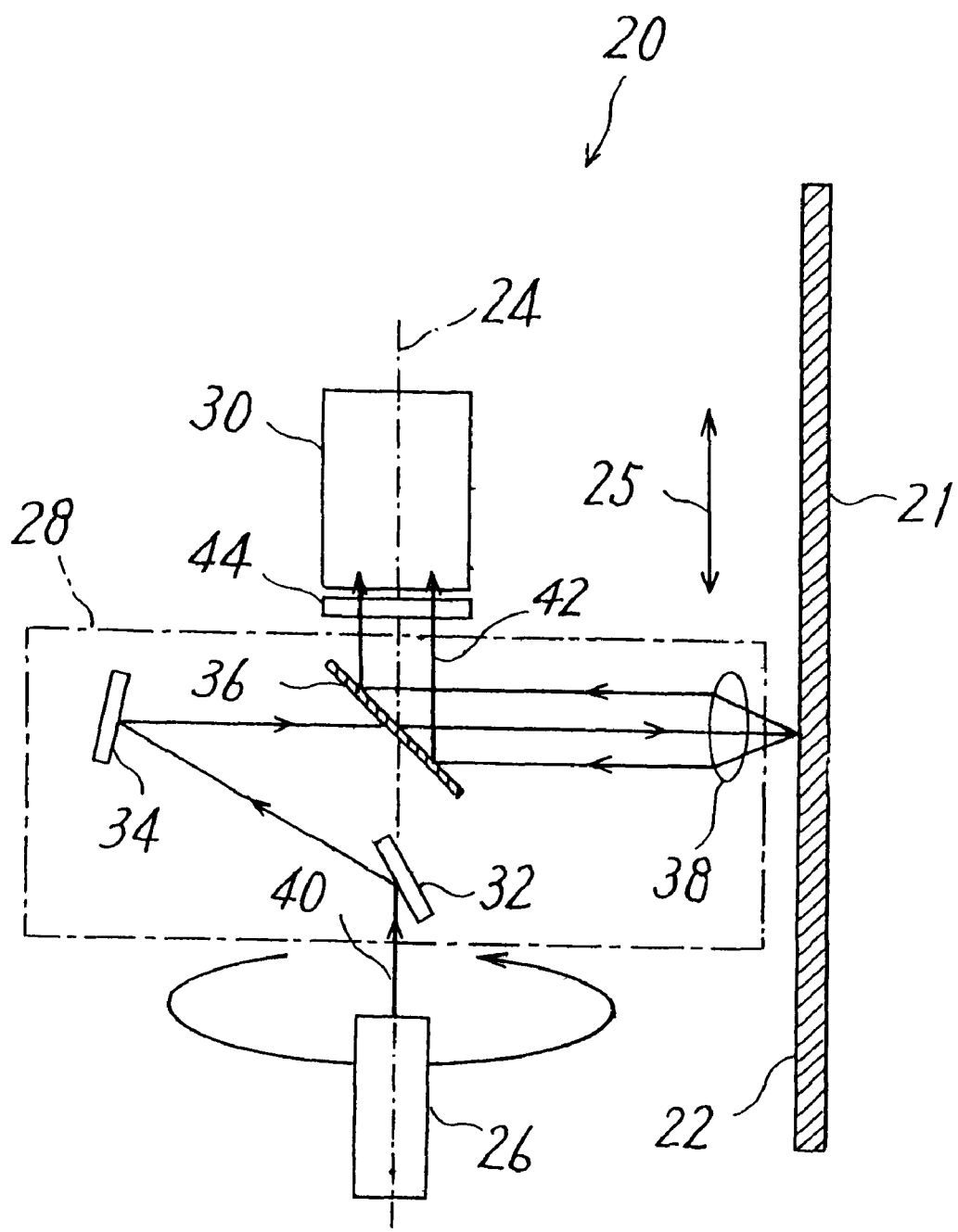
FIG. 6 is a schematic diagram showing a rotary reader for reading data of X-rays diffracted by the sample in the embodiment.

The rotary reader 20 as shown in FIG. 6 has been described by the present inventors in Japanese Patent Application Laid-Open (Kokai) No. 6-19014 and includes a laser 26, an optical reading system incorporated into a rotary member 28, and a fluorescence detector 30.

A laser beam 40 generated by the laser 26 is reflected by mirrors 32 and 34 50 as to be directed perpendicular to a recording surface 22 of the imaging plate 21 mounted on the carrier (not shown). The laser beam 40 passes through a selective mirror 36 and a condenser lens 38 and impinges on the recording surface 22 of the imaging plate 21. When a latent image is recorded on a portion of the recording surface 22 on which the laser beam 40 impinges, fluorescence is generated from the recorded portion.

The fluorescence is collected by the condenser lens 38 to become parallel rays. The parallel rays are reflected by the selective mirror 36 and thereby directed parallel to a centerline 24. Fluorescence 42 is not directed to the laser 26 but, rather, is directed toward the fluorescence detector 30, which is disposed opposite the laser 26. The fluorescence 42 passes through a filter 44, which cuts red light therefrom. The fluorescence detector 30 detects the intensity of the fluorescence 42 which has passed through the filter 44. Reference numeral 25 denotes the moving direction of the imaging plate 21 mounted on the carrier 23.

When the imaging plate 21 is transferred into the chamber 15, the rotary reader 20 reads the latent image which represents X-rays diffracted by the sample.

As shown in FIGS. 4 and 5, for example, when data of CuKα rays diffracted by the sample are recorded on the imaging plate 21 over a goniometry range 2θ of −60° to +144°, the data can be read at a speed substantially as high as that in the case of a goniometry range 2θ of ±60°, through execution of a single rotation of the rotary reader 20.

After data recorded on the imaging plate 21 is read, the data can be erased. Then, the imaging plate 21 is transferred upward in the vertical direction through operation of the drive motor 11 and is again used for recording data of diffracted X-rays.

An unillustrated controller includes the following devices: (1) sequence control for X-ray exposure, reading, and data transfer; (2) high-speed 16-bit ADC for reading data from the imaging plate; (3) RS-232C serving as a control I/F; and (4) SCSI2 serving as a data I/F.

Further, a computer for control and data processing may be provided in order to perform control and to process and display X-ray diffraction data.

Through employment of the above-described configuration, the present invention provides the following advantages.

(1) X-ray diffraction data can be collected and analyzed at high speed and high resolution. For example, the prior art (1) described above requires 3 to 4 days for collection of data, whereas the present invention enables collection of data in 3 to 4 hours.

(2) A cylindrical imaging plate is disposed vertically in an X-ray detection section in such a manner as to surround a sample, thereby collecting a large amount of X-ray diffraction data simultaneously with a resultant attainment of high speed and high resolution.

(3) The imaging plate is a two-dimensional detector (storage medium) featuring high sensitivity, broad dynamic range, and large detection (storage) area and can be used repeatedly in a semipermanent manner.

(4) The distance between an X-ray source and a sample is decreased by about 40% as compared with a conventional apparatus, thereby enhancing X-ray intensity. Measurement through use of Cu Kα rays is enabled, thereby enabling measurement with high accuracy.

(5) A broad 2θ goniometry range of −60° to +144° can be achieved through combination with a goniometer having, for example, the following rotation features: φ-axis: 360°; η-axis: −15° to 55°; and ω-axis: −85° to 265°.

The following unillustrated cooling system may be employed. A feed pipe having an outlet facing upward is disposed in such a manner as to extend toward a crystal, which serves as a sample. X-ray diffraction can be measured while a cooling gas, for example, nitrogen gas, is discharged through the outlet so as to cool the sample. Furthermore, various kinds of atmosphere can be established for the sample.

The present invention is not limited to the above-described embodiment. Numerous modifications and variations of the present invention are possible in light of the spirit of the present invention, and they are not excluded from the scope of the present invention.

As described above, the present invention produces the following effects.

(1) A space-efficient imaging-plate-type X-ray diffraction apparatus featuring an expanded 2θ goniometry range, high speed, high resolution, and design for convenient use can be provided.

(2) The above-described goniometer (1/4η goniometer) allows a crystal serving as a sample to be set such that an axis thereof is positioned vertically, without mechanical interference with the X-ray optical system and the imaging plate. Since a broad 2θ goniometry range of −60° to +144° is employed, substantially entire space data can be collected and processed even in the case where radiated X-rays are Cu Kα rays, as well as in the case of Mo Kα rays. Also, measurement through use of Cu Kα rays can attain a resolution of about 0.83 angstroms.

(3) The distance between an X-ray source and a sample is decreased by about 40% as compared with that of a conventional apparatus, thereby enhancing X-ray intensity and enabling high accuracy measurement.

As described above, the imaging-plate-type X-ray diffraction apparatus according to the present invention features a broad goniometry range, high speed, high resolution, and design for convenient use and is particularly suited for analysis of the structure of a single crystal.

What is claimed is:

1. An imaging-plate-type X-ray diffraction apparatus comprising:
   (a) means for causing a set single-crystal sample to diffract X-rays, said means comprising an X-ray optical system and a goniometer, the sample being set on the goniometer;
   (b) a single cylindrical imaging plate disposed vertically so as to record X rays diffracted by the sample, and covering a continuous 2θ goniometry range of −60° to +144°, said goniometer being disposed at a position located inside said cylindrical imaging plate and corresponding to a lower portion of said cylindrical imaging plate, without interference with the X-ray optical system and said cylindrical imaging plate, such that an axis of the sample is positioned vertically;
   (c) a cylindrical carrier providing a continuous support surface in contact with and coextensive with an outside cylindrical surface of said cylindrical imaging plate and retaining said cylindrical imaging plate;
   (d) transfer means for vertically transferring said cylindrical carrier with said cylindrical image plate retained by said cylindrical carrier; and
   (e) a rotary reader disposed so as to be coaxial with said transferred cylindrical imaging plate and adapted to read data of diffracted X-rays from an inner cylindrical surface of said cylindrical imaging plate, with said cylindrical image plate retained by said cylindrical carrier.

2. An imaging-plate-type X-ray diffraction apparatus as described in claim 1, wherein radiated X rays are Cu Kα rays.

* * * * *

UNITED STATES PATENT AND TRADEMARK OFFICE
CERTIFICATE OF CORRECTION

PATENT NO. : 6,418,190 B1
DATED : July 9, 2002
INVENTOR(S) : Yokozawa et al.

Page 1 of 1

It is certified that error appears in the above-identified patent and that said Letters Patent is hereby corrected as shown below:

Title page,
Item [56], FOREIGN PATENT DOCUMENTS, "64-147858" should read
-- 62-147858 --.

Column 3,
Line 52, "50" should read -- so --.

Column 4,
Line 53, "$\eta$-axis" should read -- $\chi$-axis --.

Column 5,
Line 7, "(1/4$\eta$" should read -- (1/4$\chi$ --.

Signed and Sealed this

Twenty-ninth Day of October, 2002

Attest:

*Attesting Officer*

JAMES E. ROGAN
*Director of the United States Patent and Trademark Office*